United States Patent
Srinivasan et al.

(10) Patent No.: US 11,883,140 B2
(45) Date of Patent: Jan. 30, 2024

(54) TACTILE BLOOD PRESSURE IMAGER

(71) Applicants: Trustees of Tufts College, Medford, MA (US); Massachusetts Institute of Technology, Cambridge, MA (US)

(72) Inventors: Mandayam A. Srinivasan, Newton, MA (US); Mohan Thanikachalam, Boston, MA (US); Edward Howard Adelson, Winchester, MA (US); Abhijit Biswas, Shyamnagar (IN)

(73) Assignees: Trustees of Tufts College, Medford, MA (US); Massachusetts Institute of Technology, Cambridge, MA (US)

( * ) Notice: Subject to any disclaimer, the term of this patent is extended or adjusted under 35 U.S.C. 154(b) by 435 days.

(21) Appl. No.: 17/044,321

(22) PCT Filed: Mar. 29, 2019

(86) PCT No.: PCT/US2019/025011
§ 371 (c)(1),
(2) Date: Sep. 30, 2020

(87) PCT Pub. No.: WO2019/195120
PCT Pub. Date: Oct. 10, 2019

(65) Prior Publication Data
US 2021/0153755 A1  May 27, 2021

Related U.S. Application Data

(60) Provisional application No. 62/684,726, filed on Jun. 13, 2018, provisional application No. 62/652,180, filed on Apr. 3, 2018.

(51) Int. Cl.
*A61B 5/022* (2006.01)
*A61B 5/02* (2006.01)
(Continued)

(52) U.S. Cl.
CPC ...... *A61B 5/02233* (2013.01); *A61B 5/02007* (2013.01); *A61B 5/1075* (2013.01);
(Continued)

(58) Field of Classification Search
CPC . A61B 5/6885; A61B 5/6886; A61B 5/02233; A61B 5/02007; A61B 8/0891;
(Continued)

(56) References Cited

U.S. PATENT DOCUMENTS 4,245,648 A   1/1981   Trimmer
4,869,261 A   9/1989   Penaz
(Continued)

FOREIGN PATENT DOCUMENTS

EP   1 204 370 B1   4/2008
JP   2006-280485 A   10/2006
(Continued)

OTHER PUBLICATIONS

International Search Report and Written Opinion for International Patent Application No. PCT/US2019/025011, dated Jun. 26, 2019 (13 pages).
(Continued)

*Primary Examiner* — Eric F Winakur
*Assistant Examiner* — Emily C Clement
(74) *Attorney, Agent, or Firm* — Nixon Peabody LLP

(57) ABSTRACT

A method is directed to continuously, non-invasively, and directly measuring blood pressure, and includes providing a calibrated measurement device having a blood-flow control balloon and a sensor array. The method further includes placing the sensor array in a non-invasive manner over the surface of a patch of skin connected to an artery by adjoining soft tissues and inflating the blood-flow control balloon with a controlled amount of pressure. In response to the inflating of the blood-flow control balloon, changes in the artery
(Continued)

geometry and forces are detected, via the sensor array, during a heartbeat cycle. The changes correspond to spatio-temporal signals from the artery or in the adjoining soft tissues. The spatio-temporal signals are measured and processed, via a controller, to determine blood-pressure parameters.

20 Claims, 14 Drawing Sheets

(51) Int. Cl.
    *A61B 5/107*         (2006.01)
    *A61B 8/08*          (2006.01)

(52) U.S. Cl.
    CPC .......... *A61B 5/1079* (2013.01); *A61B 8/0891* (2013.01); *A61B 2560/0223* (2013.01); *A61B 2562/0214* (2013.01); *A61B 2562/04* (2013.01)

(58) Field of Classification Search
    CPC ................ A61B 5/1075; A61B 5/1079; A61B 2560/0223; A61B 2562/0214; A61B 2562/04; A61B 5/02141; A61B 5/02255; A61B 5/02116; A61B 5/681; A61B 5/6843; A61B 8/4416; A61B 5/022; A61B 8/04; A61B 2562/0233; A61B 2562/0247; G01L 1/24
See application file for complete search history.

(56) References Cited

U.S. PATENT DOCUMENTS

| | | |
|---|---|---|
| 2005/0171443 A1 | 8/2005 | Gorenberg |
| 2006/0206031 A1 | 9/2006 | Hasegawa |
| 2009/0315989 A1 | 12/2009 | Adelson |
| 2010/0106016 A1* | 4/2010 | Orbay ................. A61B 8/4227 600/494 |
| 2012/0197128 A1* | 8/2012 | Palti ..................... A61B 5/0816 600/453 |
| 2015/0062018 A1 | 3/2015 | Naidu |
| 2016/0287103 A1* | 10/2016 | Saponas ............... A61B 5/6824 |
| 2017/0340209 A1 | 11/2017 | Klaassen |

FOREIGN PATENT DOCUMENTS

| | | |
|---|---|---|
| RU | 2638712 C1 | 12/2017 |
| SU | 202437 A1 | 1/1967 |
| SU | 685275 A1 | 9/1979 |
| WO | WO 00/72750 A1 | 12/2000 |
| WO | WO 2014/030174 A2 | 2/2014 |
| WO | WO 2018/025280 A2 | 2/2018 |

OTHER PUBLICATIONS

Johnson, M. et al.; "Retrographic sensing for the measurement of surface texture and shape"; Jun. 20-25, 2009 IEEE Conference on Computer Vision and Pattern Recognition, pp. 1070-1077 (8 pages).
Supplementary Partial European Search Report in European Patent Application No. EP 19781541.8, dated Jan. 28, 2022 (8 pages).
Search Report in Russian Patent Application No. RU 2020131254/14, dated Jul. 20, 2022 (4 pages w/English translation).
European Search Report for European Patent Application No. 22 21 3084.1, dated Mar. 3, 2023 (7 pages).

\* cited by examiner

| ID | MPF | SFR | IAH | MPFh | SFRh | IAHh | IARh | IARh | SID | SCP | SDP | SF1 | SF2 |
|---|---|---|---|---|---|---|---|---|---|---|---|---|---|
| GN | 0 | 1 | 2 | 6 | 7 | 8 | 9 | 10 | 11 | 12 | 13 | 15 | 16 |
| AV | 1.00 | 0.30 | 1.00 | 19.03 | 6.73 | 8.0 | 4.76 | 4.76 | 0.40 | 2.00 | 0.20 | 0.40 | 0.15 |
| DP | 123.9 | 450.3 | -105.0 | -0.0 | -0.1 | -0.0 | -0.0 | -0.1 | 2.6 | 0.0 | 0.0 | 3.7 | -2.6 |
|    | 13.7 | 54.3 | 5.9 | 1.9 | 26.3 | 0.9 | 3.4 | 0.8 | 324.6 | 0.0 | 0.0 | 275.1 | 259.3 |
| RT | 0.0 | 0.00 | 0.0 | 0.0 | 0.0 | 0.0 | 0.0 | 0.0 | 0.0 | 0.0 | 0.0 | 0.0 | 0.0 |

FIG. 3D

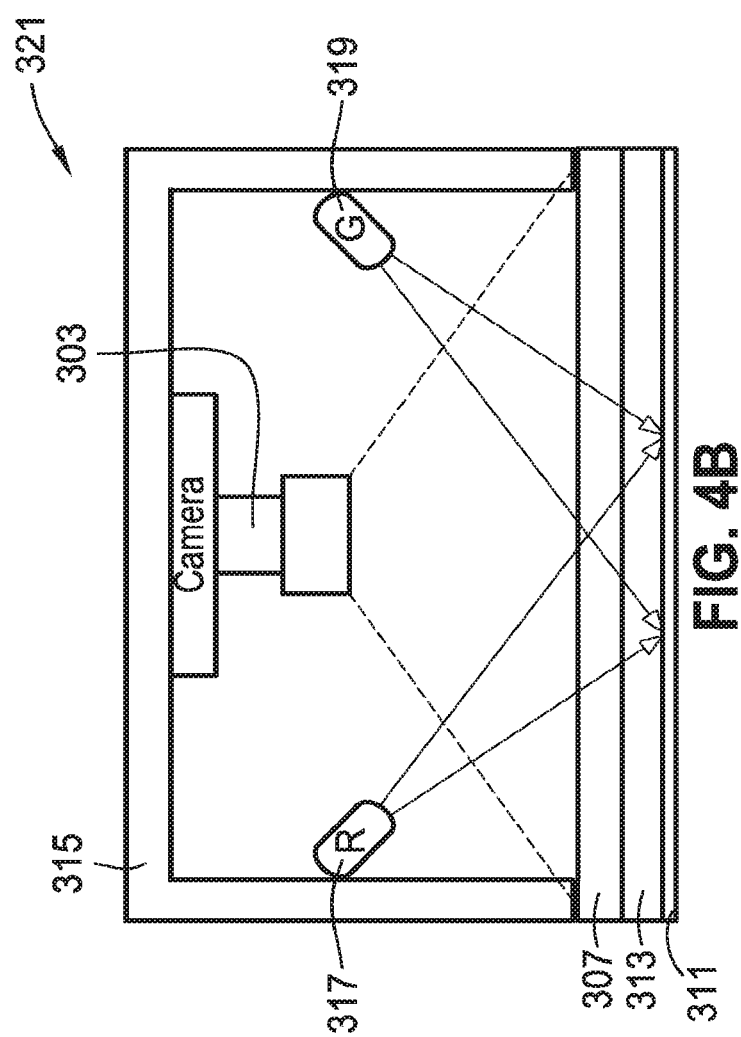

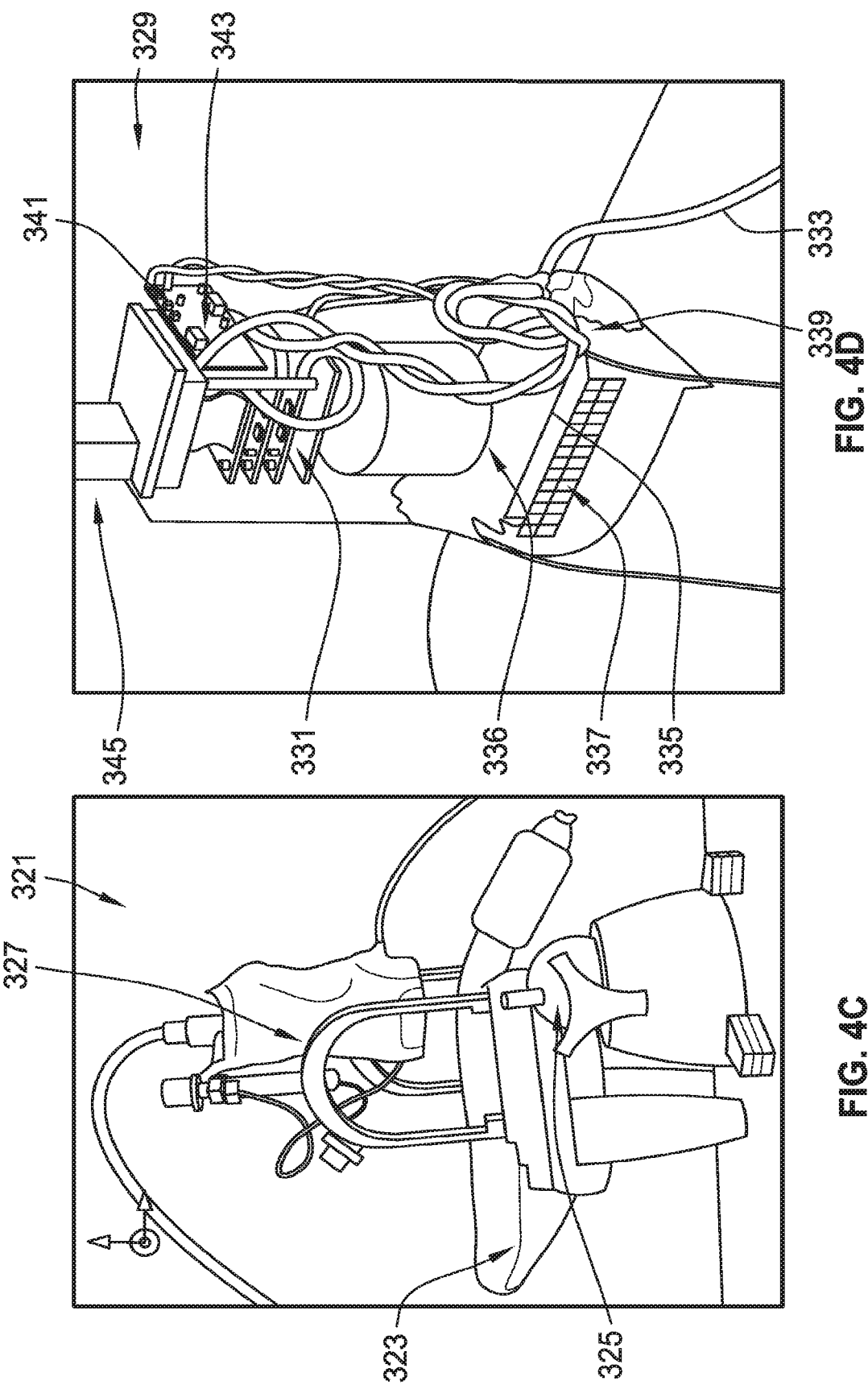

TACTILE BLOOD PRESSURE IMAGER

CROSS-REFERENCE TO RELATED APPLICATIONS

This application is a U.S. National Stage of International Application No. PCT/US2019/025011, filed on Mar. 29, 2019, which claims priority to U.S. Provisional Patent Application No. 62/684,726, filed Jun. 13, 2018, and U.S. Provisional Patent Application Ser. No. 62/652,180, filed Apr. 3, 2018, each of which is hereby incorporated by reference herein in its entirety.

GOVERNMENT SUPPORT

This invention was made with government support under grant no. 1 U01 EB018823001A1 awarded by the National Institutes of Health (NIH). The government has certain rights in the invention.

FIELD OF THE INVENTION

The present invention relates generally to a non-invasive estimation and continuous monitoring of arterial blood pressure, and, more specifically, to the use of skin surface displacements and forces for directly measuring and monitoring the arterial blood pressure.

SUMMARY OF THE INVENTION

According to one aspect of the present disclosure, a method is directed to continuously, non-invasively, and directly measuring blood pressure, and includes providing a calibrated measurement device having a blood-flow control balloon and a sensor array. The method further includes placing the sensor array in a non-invasive manner over the surface of a patch of skin connected to an artery by adjoining soft tissues and inflating the blood-flow control balloon with a controlled amount of pressure. In response to the inflating or deflating of the blood-flow control balloon, changes occur in the artery size and shape, and in the forces the artery applies on the surrounding tissue. Consequently, a change occurs in the contact between the skin and the sensor array that is detected, via the sensor array, during a heartbeat cycle. The changes in artery geometry and artery forces correspond to spatio-temporal signals from the artery. The spatio-temporal signals are measured and processed, via a processor, to determine blood-pressure parameters.

According to another aspect of the present disclosure, a calibrated measurement device is directed to continuously, non-invasively, and directly measuring blood pressure. The calibrated measurement device includes a strap, a blood-flow control balloon coupled to the strap, the blood-flow control balloon having an inflated state in which a controlled amount of pressure isolates a spatio-temporal signal from an artery without compromising venous and lymphatic circulation or flow in other arteries of a limb. The calibrated measurement device further includes a sensor array on the surface of the blood-flow control balloon to non-invasively and directly measure and monitor blood pressure. The sensor array detects changes in the artery geometry and forces during a heartbeat cycle and when the blood-flow control balloon is in the inflated state. The changes correspond to spatio-temporal signals from the artery.

Optionally, in the above aspect of the present disclosure, the sensor array is implemented based on a gel membrane with a painted surface, with a structured light or with optical markers mounted on an outside surface of the blood-flow control balloon. However, in another exemplary aspect of the present disclosure, the sensor array is implemented based on a painted surface, with optical markers or a structured light pattern on the material of the blood-flow control balloon on its inside surface or on the outside surface. Further, in another exemplary aspect of the present disclosure, the sensor array is implemented based on optical markers or a structured light pattern projected directly on the skin surface.

In accordance with another exemplary aspect of the present disclosure, a sensor array is implemented based on deformation sensing by photometric stereo with the help of gel membrane with a painted surface and colored lights. Optionally, another exemplary aspect is directed to a sensor array that is implemented based on discrete force or displacement sensors. Specifically, the sensor array is implemented by assembling discrete force or deformation sensors such as resistive, piezoelectric, or capacitive elements.

Optionally, in one or more of the above-described aspects of the present disclosure, a gel membrane is mounted on an outside surface of the blood-flow control balloon. However, in another exemplary aspect of the present disclosure, the gel membrane is replaced by a painted surface or a structured light pattern on the material of the blood-flow control balloon on its inside surface or on the outside surface.

According to yet another alternative exemplary embodiment, a sensor is coupled to a mechanical stage and is used for varying a mounting force (e.g., in a bench top device). In this embodiment, instead of using a blood-flow control balloon, the mounting force is adjusted with the help of a mechanical stage that is coupled with force and/or displacement sensors.

To additionally modulate the contact conditions, the blood-flow control balloon is added together with (1) a pressure sensor that provides a direct measure of the spatial average of forces on a patch of contact with the object (with or without the gel membrane), (2) an air pump that is used to actively change the contact conditions (e.g., geometrical and force changes), and (3) a controller that provides a degree of control over contact conditions and their changes over time, particularly with feedback from the pressure sensor. Gels or other fluids other than air filling the blood-flow control balloon are optionally considered based on respective measurement tasks.

According to yet another aspect of the present disclosure, a method is directed to continuously, non-invasively, and directly measuring blood pressure in an artery. The method includes providing a calibrated measurement device having strap for mounting on a limb, the strap having mounted on its internal surface a blood-flow control balloon, a strap control balloon, and a strap force sensor. The blood-flow control balloon has mounted on its internal surface a sensor array. The method further includes placing the strap over a limb such that the sensor array is in contact with a skin surface over an artery in a non-invasive manner, and inflating the blood-flow control balloon with a controlled amount of pressure without compromising venous and lymphatic circulation or flow in other arteries of the limb. In response to inflating the blood-flow control balloon, the method further includes detecting, via the sensor array, changes in the artery geometry and forces during a heartbeat cycle, the changes corresponding to spatio-temporal signals from the artery. The strap control balloon is inflated with a controlled amount of pressure to apply a force between the strap and the skin surface. Based on detection by the sensor array and the strap force sensor, fine-tuning pressure is applied by at least one of the blood-flow control balloon or the strap control balloon to enhance detection of the spatio-temporal signals from the artery. The spatio-temporal signals are measured and processed, via a processor, to determine blood-pressure parameters.

Additional aspects of the disclosure will be apparent to those of ordinary skill in the art in view of the detailed description of various embodiments, which is made with reference to the drawings, a brief description of which is provided below.

BRIEF DESCRIPTION OF THE DRAWINGS

FIG. 3D shows a fourth portion of data related to the spatio-temporal signals and blood pressure markers of FIG. 3A, the data including values for various signals.

FIG. 4B shows a camera setup of the calibrated measurement device of FIG. 4A with light-emitting diode (LED) regulators.

FIG. 4C is a perspective view illustrating a bench-top version of the calibrated measurement device of FIG. 4A.

FIG. 4D is a perspective view illustrating a wearable version of the calibrated measurement device of FIG. 4A.

Figure 1:
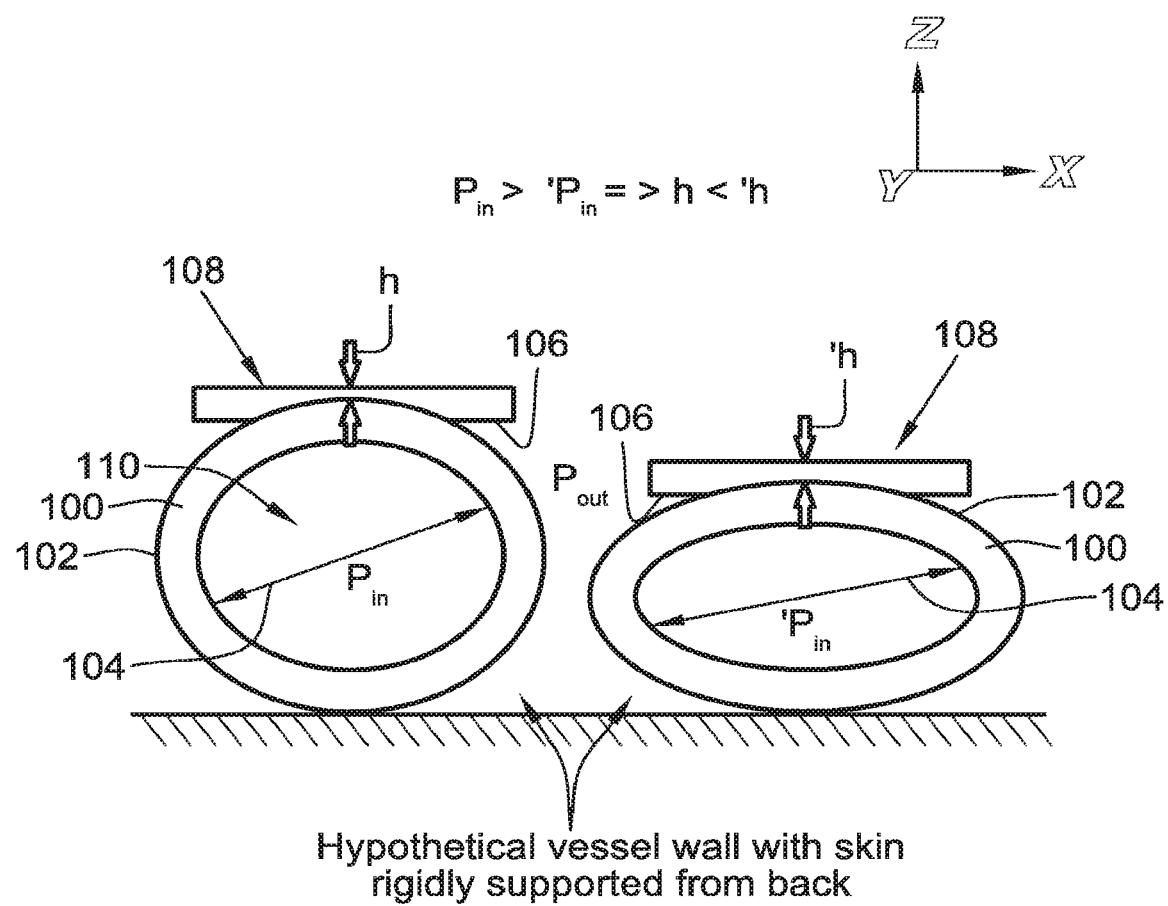
FIG. 1 is a schematic illustration showing changes in curvature of a vessel wall.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DETAILED DESCRIPTION

The present disclosure is generally directed to a novel approach, several methods, and associated instrument configurations to estimate and continuously monitor intra-arterial blood pressure (BP) over time. Based on the disclosed methodology, direct measurements are made for systolic blood pressure (SBP), mean arterial blood pressure (MAP) and diastolic blood pressure (DBP). A Tactile Blood Pressure Imager (TBPI), also referred more generally to as a Blood Pressure Imager (BPI), is used to measure beat-to-beat variability in SBP, MAP, and DBP, including respiratory variance in blood pressure, over time. Based on this, the TBPI is able to identify abnormal blood pressure patterns, such as, white coat hypertension, masked hypertension, and non-dipping and other abnormal patterns during sleep and morning blood pressure surge. The TBPI facilitates accurate assessment of treatment effectiveness and better tailoring of therapy, and further identifies lifestyle motivations, such as for reducing smoking and stress, needed to lower patients' blood pressure. The TBPI continuously tracks heart rate (HR) and, thus, HR variability, and any abnormal heart rhythms over time. The BPI also continuously tracks respiration rate (RR) and abnormal respiratory patterns. The TBPI further tracks beat-to-beat blood pressure and is a non-invasive alternative to invasive intra-arterial blood pressure monitoring.

Referring to FIG. 1, a schematic illustration shows how a change of blood pressure changes the curvature of a vessel wall 100 and, hence, a skin surface 102. Blood pressure has a direct relationship to an artery size and shape (for example, diameter 104), which, in turn, govern the spatial distribution of deformations of and forces on a contact surface 106 of a force or deformation sensor array 108. The sensor array 108 is in contact with the skin surface 102, particularly at locations of superficial arteries 110, such as the radial artery at the wrist. Dynamics of the blood pressure inside the artery 110 impose spatio-temporal dynamics in a contact surface profile. This basic principal is used to estimate and track blood pressure continuously.

If the sensor array 108 is mounted and pressed on top of the skin surface 102 over a superficial blood vessel 110, the sensor array 108 captures the variation of the arterial cross-sections over space and time. The blood pressure has a direct relationship with the shape and size of the arterial cross-sections, which in turn governs the contact surface profile (spatial distribution of deformation and forces) in-between the skin surface 102 and the sensor array 108. Thus, dynamics of the blood pressure inside the vessel impose spatio-temporal dynamics in the contact surface profile that can be measured noninvasively.

Figure 2:
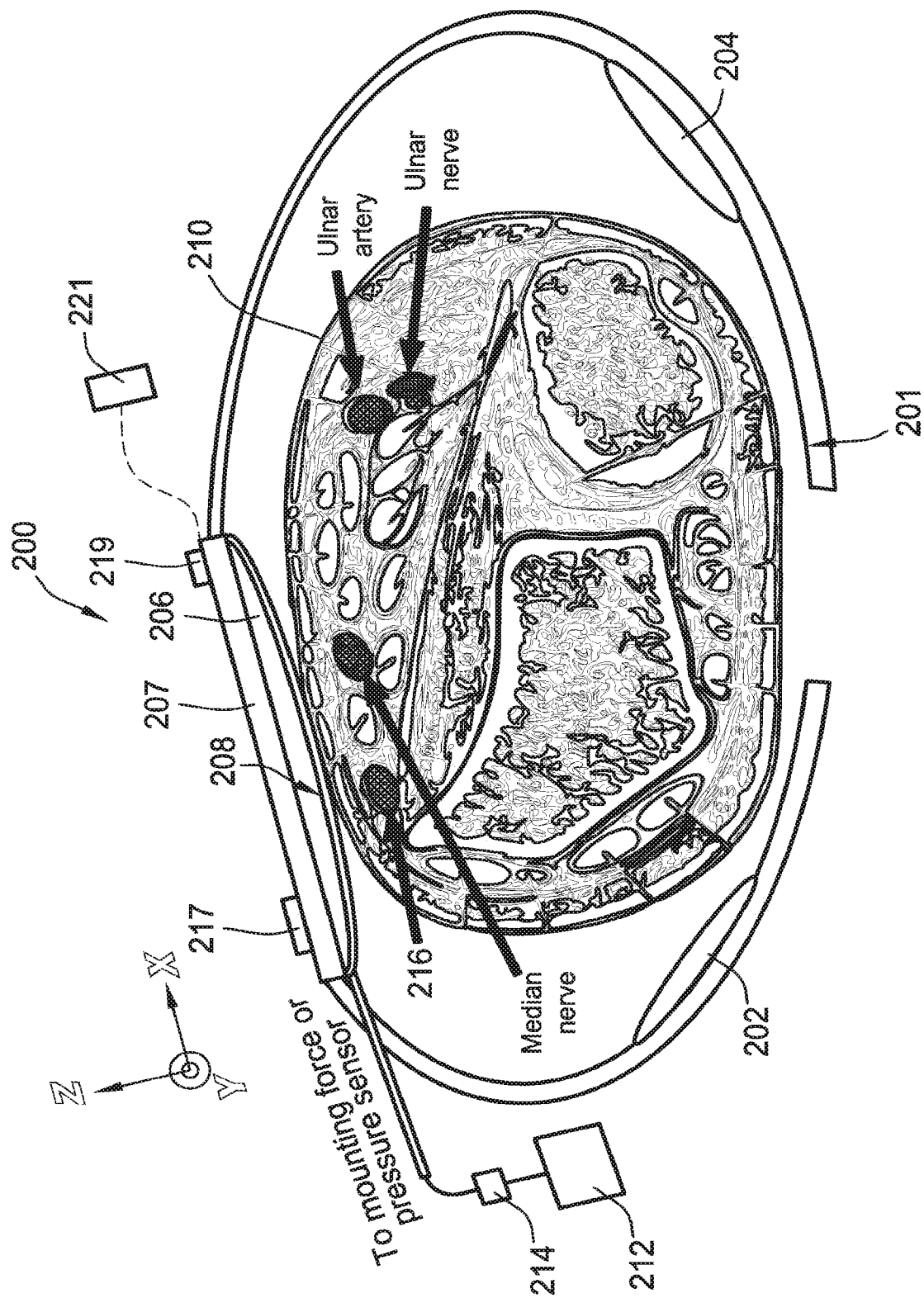
FIG. 2 is a cross-sectional illustration showing components of a calibrated measurement device, according to one embodiment of the present disclosure.
Figure 3A:
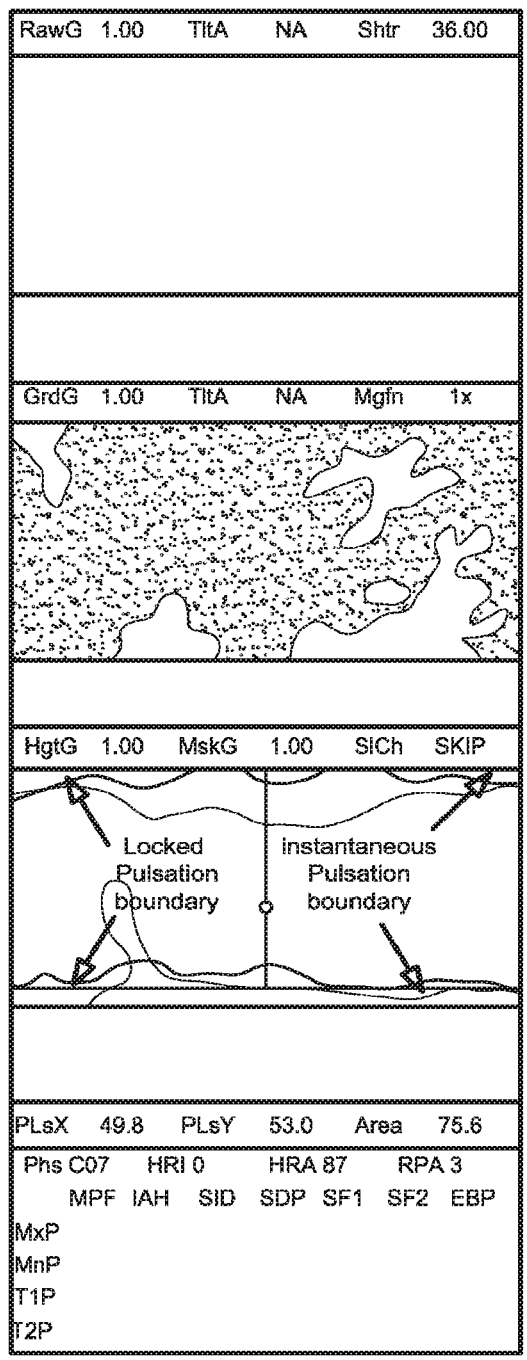
FIG. 3A shows a first portion of data related to spatio-temporal signals and blood pressure markers, the data including raw spatial information, processed spatial information, and a height image.
Figure 3B:
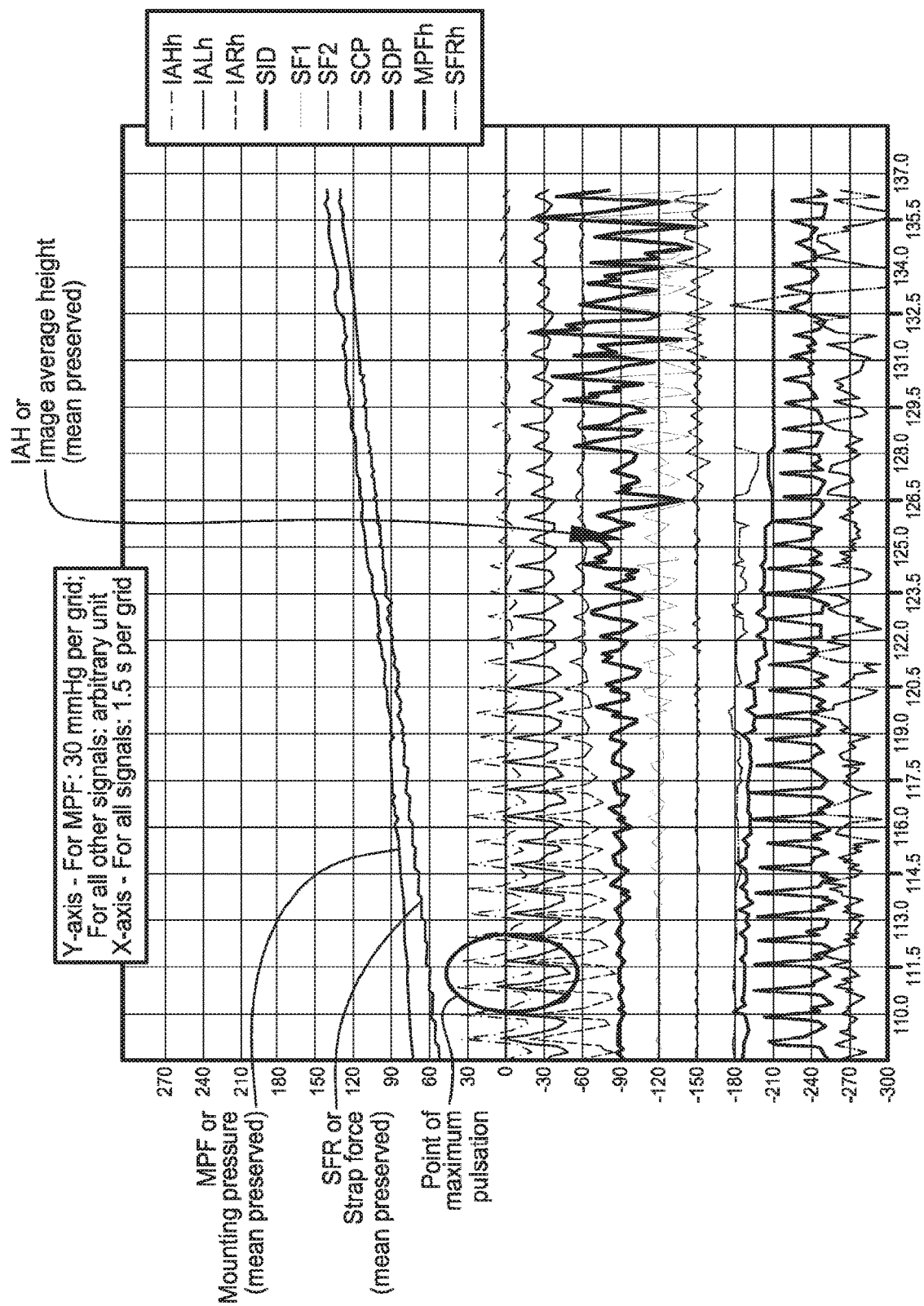
FIG. 3B shows a second portion of data related to the spatio-temporal signals and blood pressure markers of FIG. 3A, the data including plots for various signals.
Figure 3C:
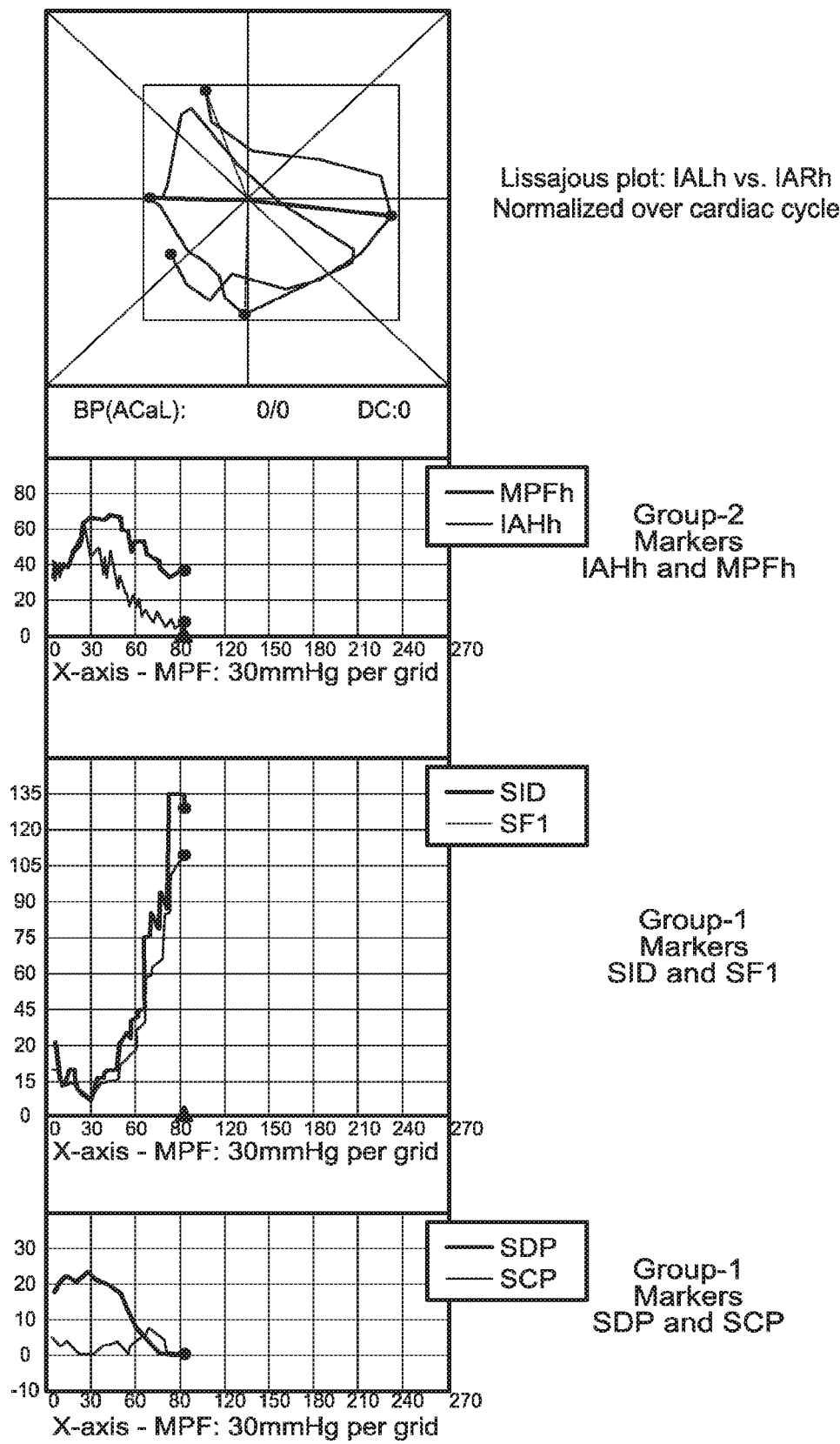
FIG. 3C shows a third portion of data related to the spatio-temporal signals and blood pressure markers of FIG. 3A, the data including plots of group markers.

Referring to FIG. 2, a TBPI is in the form of an exemplary calibrated measurement device 200 that includes a flexible strap 201 containing (1) a strap force sensor (SFS) 202, which is a force sensitive resistor (SFR), (2) a strap control balloon 204 for tightness adjustment of the strap 200, and (3) a blood-flow control balloon 206, also referred to as a mounting force adjustment balloon (MFAB), which is mounted to a rigid support 207. A sensor array 208 is interfaced between the blood-flow control balloon 206 and a skin surface 210 to capture spatio-temporal contact conditions. The blood-flow control balloon 206 is actuated by an air pump 212, and an air pressure sensor 214 connected to the air pump 212 acts as the sensor for the blood-flow control balloon 206.

Optionally, the device 200 includes a controller 217 (with a processor and memory device) configured to receive signals from the strap force sensor 202 and/or the sensor array 208. The controller 217 is further optionally configured to process the signals to determine parameters of blood pressure, including estimation and monitoring of blood pressure. The controller 217 is integrated with the device 200, e.g., mounted to or placed within the strap 201, or is a separate component from the device 200, e.g., it is an external device (such as a computer) communicatively coupled to the device 200.

According to another optional configuration, the device 200 includes a display 219 for displaying various parameters associated with monitoring of blood pressure. The display 219 is optionally mounted to or integrated with the device 200.

According to another optional configuration, the device 200 is communicatively coupled to an external device 221, such as a mobile phone of a user. The user uses an application on the mobile phone 221 to perform one or more tasks associated with the device 200, including, for example, controlling inflation of the strap control balloon 204 and/or the blood-flow control balloon 206, receiving parameters of the monitored artery, etc.

The blood-flow control balloon 206 is initialized to a reference air pressure (e.g., 30-40 mmHg). Then, the blood-flow control balloon 206 and the sensor array 208 are placed above a peripheral artery 216 (e.g., the radial artery at the wrist) such that the sensor array 208 is approximately centered over the artery 216 so that it captures the pulsation (variation of spatio-temporal contact condition caused by variation of blood pressure over a cardiac cycle) at a central region of the sensor array 208, while the blood-flow control balloon 206 controls the blood flow in the artery 216 underneath.

Subsequently, the strap control balloon 204 is inflated to a level such that the reading from the strap force sensor 202 reaches a certain value. Based on the spatial information obtained from the sensor array 208, the dominant pulsating area is locked. The dominant pulsating area is the one in which temporal dynamics are above certain threshold, when the blood-flow control balloon 206 and the strap force sensor 202 are adjusted to an optimum predetermined value. The strap control balloon 204 and the strap force sensor 202 are primarily used for fine tuning the mounting of the calibrated measurement device 200 to ensure optimal contact of the sensor array 208 with the skin surface 210, and for standardization of mounting the calibrated measurement device 200 across subjects. Signals obtained from the strap force sensor 202 and the strap control balloon 204 are used for blood pressure estimation and monitoring.

One beneficial and unique aspect of the calibrated measurement device 200 is the effective isolation of the primary measurement and manipulation area over the targeted artery 216 from the rest of the area under the strap 201. The achieved isolation eliminates the need for a complete cuff around the limb. The unique design of the calibrated measurement device 200 enables continuous use of the calibrated measurement device 200 on a limb without compromise to the venous and lymphatic circulation or to flow in other arteries of the limb. The sensor array 208, which is positioned between the blood-flow control balloon 206 and the skin surface 210 captures the spatio-temporal contact conditions as the blood-flow control balloon 206 inflates and deflates during blood pressure estimation phase, and subsequently maintains a nominal pressure during blood pressure monitoring phase.

Referring to FIGS. 3A-3D, data shows estimated spatio-temporal signals and blood pressure markers. After TBPI mounting is standardized, the TBPI (such as the calibrated measurement device 200) is calibrated by estimating a user's DBP, MAP, and SBP. This is achieved by using the TBPI itself. The calibration process involves gradual increase and decrease of the pressure in MFAB, which is termed as pressure sweep. In the rising sweep the air pressure in MFAB is gradually increased from a low value (~30 mmHg) at a rate standard for conventional blood pressure measurement (2-4 mmHg/s). The rising sweep continues until the air pump saturates (~270 mmHg) or the pulsation amplitude of the measured signals is attenuated below a certain threshold provided it reaches some nominal value (e.g., 180 mmHg). Then, in falling sweep the air pressure is decreased back to the low pressure (~30 mmHg). This enables blood pressure calibration and estimation twice over a complete sweep.

To shorten the calibration time, either the rising or falling half of the sweep can be rapid, while the calibration is performed on the slower half. For estimation of blood pressure from the sweep, the mean pressure (averaged over cardiac cycle) in MFAB, termed "MFAB pressure," is considered as primary measurement for blood pressure estimation. The different features of the spatio-temporal signal from the underlying sensor array are considered as markers for SBP or MAP or DBP estimation. The MFAB pressure at which the markers reach certain thresholds are mapped to either SBP or MAP or DBP. The markers used in the blood pressure estimation method are classified in two groups. The markers in Group-1 are the spatial match/mismatch of pulsation over a cardiac cycle within the contact region between the skin and the sensor array. The markers in Group-2 are the amplitude of the pulsation averaged over space. Markers from both Group-1 and Group-2 are estimated simultaneously over any half-sweep. The blood pressure estimation based on multiple markers is combined to improve accuracy and robustness of the final blood pressure estimation.

Referring to Group-1 markers, the spatial information from the locked pulsating area is split into proximal and distal regions in relation to heart or direction of blood flow in the vessel (e.g., Y axis of FIG. 1). After segmentation, the average height of the pulsation is calculated for proximal and the distal halves individually. These two temporal signals effectively represent the proximal and distal pressure waves. After high-pass filtering and normalizing of their heights over the past cardiac cycle, their similarity and dissimilarity between proximal and distal regions are considered as the blood pressure markers. Estimating these blood pressure markers is a beneficial and unique application of the TBPI. The Group-1 markers are basically dependent on the spatial information of the pressure wave. To quantitatively measure the similarity between the proximal and distal pressure waves, the dot-product of the proximal and distal pressure waves is calculated over the duration of the most recent cardiac cycle and is estimated in real-time. The marker is termed as a selected dot-product (SDP). While SDP is a quantitative measure of similarity, a selected cross-product (SCP) is one measure of dissimilarity that is graphically represented as the area under a Lissajous plot of normalized proximal vs. distal pressure wave.

Another approach of measuring dissimilarity quantitatively is to compute a selected instantaneous difference (SID) signal of the normalized proximal and distal pressure waves and, then, to consider the height of the SID over a cardiac cycle as a blood pressure marker. SID is also passed through different band-pass filters to capture the higher harmonics originated due to turbulent blood flow in the artery when it starts collapsing. These signals are termed as SF1, SF2, and so on, and corresponding blood pressure markers are calculated similar to SID (see FIG. 2).

Referring to Group-2 markers, the first markers in this group provide the deformation or force information obtained from the sensor array averaged over space, termed as image average height (IAH) and passed through a high pass filter and amplitude estimator. The amplitude estimation is performed over the duration of the most recent cardiac cycle. The Group-2 markers do not fundamentally depend on the spatial information of the pressure wave. However, because these markers are derived from the dominant pulsating area, the markers use the spatial information as obtained from the sensor array. The MFAB pressure at which Group-2 markers reach the maximum is mapped to MAP. The air pressure range through which the markers remain above certain threshold(s) indicates the intra-arterial pulse pressure (PP) that is the difference between SBP and DBP. Thus, focusing on the falling half of the sweep, the MFAB pressure at which the markers cross a certain "first-falling" threshold is mapped to SBP. After reaching the maximum, the markers again cross another "second-falling" threshold and the corresponding MFAB pressure is mapped to DBP.

The Group-2 markers are also directly obtained from the MFAB pressure signal passed through a high-pass filter and an amplitude estimator. Over a half sweep the mean or low-pass filtered MFAB pressure at which any of these markers reaches maximum is mapped to MAP. The range of mean MFAB pressure through which the markers remain above certain threshold(s) indicates the intra-arterial PP. Thus, focusing on the falling half of the sweep, the mean MFAB pressure at which a marker crosses a certain first-falling threshold is mapped to SBP. After reaching the maximum, the marker again crosses the same or a different second-falling threshold and the mean MFAB pressure corresponding to that is mapped to DBP. The markers of Group-2 are derived from the high-pass filtered MFAB pressure and are similar to the markers of a standard oscillometric method except that in TBPI the MFAB pressure signal is obtained from an isolated patch of skin region connected by soft tissues to the artery instead of the skin region covering the entire circumference of a limb, as in the case of traditional blood pressure cuffs.

The blood pressure is continuously tracked using the TBPI. After the calibration of the TBPI is complete, the pressure in the MFAB is increased back to a level so that the pulsation in the captured signals reaches certain amplitude or signal to noise ratio (SNR). Under this condition, IAH is calibrated over two points: a maximum is mapped to SBP and a minimum to DBP as obtained from a calibration method. This two-point calibration is sufficient to identify the small variation of blood pressure over the operating point. If the operating point shifts above a threshold, which may be caused by a large change of the blood pressure or based on an artifact invalidating the linear calibration to a great extent, a recalibration is performed. Instead of IAH, the pressure signal from MFAB is also calibrated and used for continuous monitoring. However, IAH shows lower sensitivity to motion and material relaxation related artifacts.

Figure 4A:
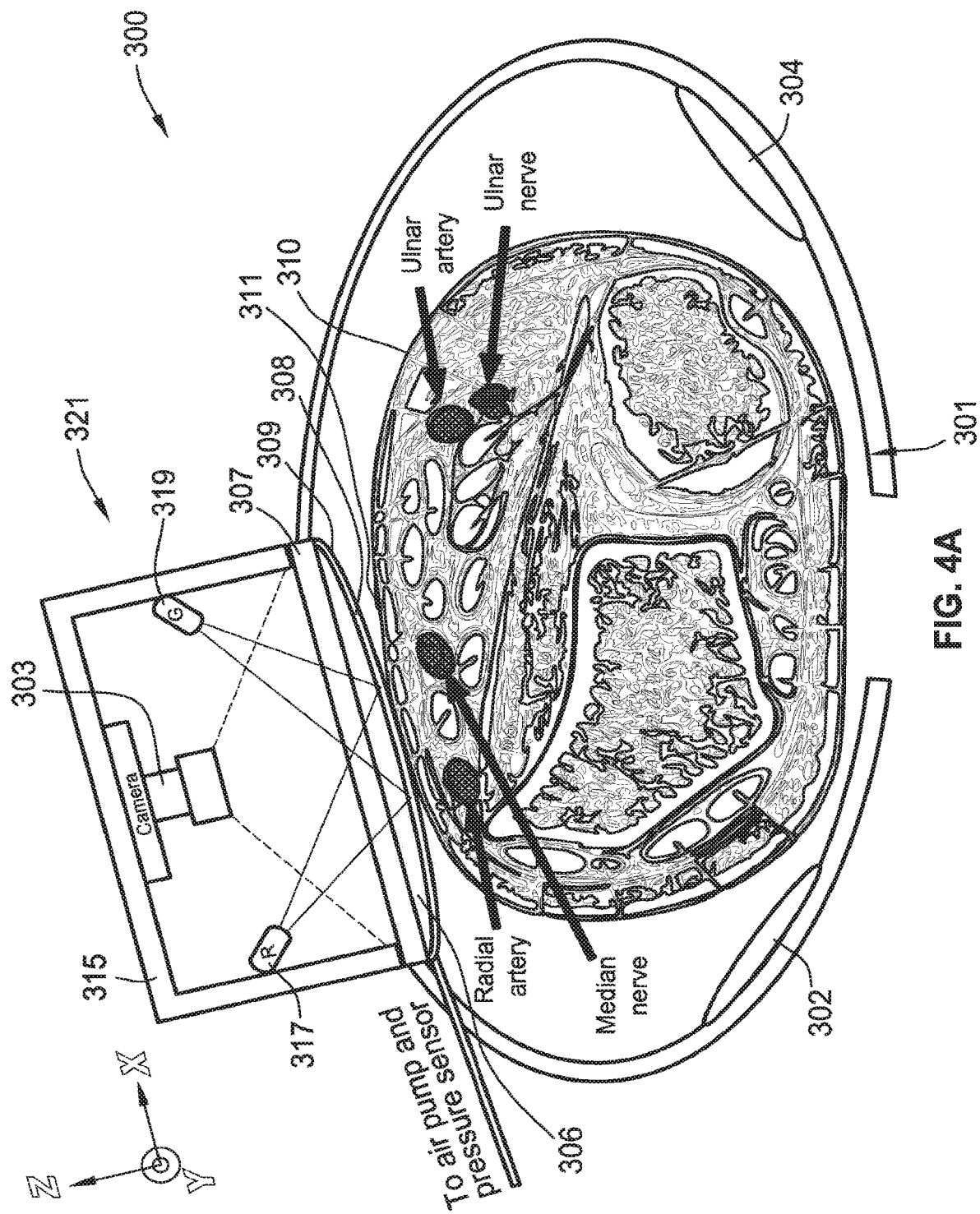
FIG. 4A is a cross-sectional illustration showing components of a calibrated measurement device including a camera, according to another embodiment of the present disclosure.

Referring to FIGS. 4A and 4B, a TBPI is in the form of another exemplary calibrated measurement device 300 in which a sensor array 308 is implemented based on deformation sensing with the help of a photometric stereo effect captured by a camera 303. The device 300 contains a flexible strap 301, a strap force sensor 302, a strap control balloon 304, and a blood-flow control balloon 306 supported on a transparent rigid support (such as glass) 307. In this embodiment, a sensor surface 309 is in contact with a skin surface 310, which is coated with pigment, such as bronze dust, that creates a specular reflective layer 311. A transparent and soft silicone elastomer (such as gel) is used as the substrate of the reflective layer 311. The gel is supported by the glass support 307 such that the reflective surface of the gel remains in close contact to the skin surface 310. The camera 303 is mounted perpendicularly on a frame 315 above the glass support 307.

As shown in FIG. 1, curvature of the blood vessel 110 along a ZX plane changes with difference between Pin and the ambient pressure Pout. Therefore, the primary measurement in this embodiment is the ZX plane curvature of the contact surface 309 and its variation along they Y-axis, i.e., the longitudinal axis of the blood vessel. Thus, two arrays of highly directional (~15° beam angle) red and green LEDs 317, 319 are placed along the Y-axis. The full camera assembly 321 is optically isolated from ambient light. To avoid the camera 303 capturing the direct reflection of the LEDs 317, 319 from the optical interfaces, the LEDs 317, 319 are placed at a low grazing angle.

Referring to FIG. 4C, a bench-top version 321 of the calibrated measurement device 300 includes 5 or 6 degree of freedom positioners and an adjustable back support 323 together with a ball-socket joint 325. The back-support can support a phantom artery or an animal body part or the human wrist. In all the cases, the system has at least a mounting force or pressure (MPF) sensor. In bench-top experiments MPF sensing is done with 6-DoF force sensors or with a force sensitive resistor (FSR). The bench-top version 321 further has a version of TBPI, such as the wearable part 327 described below.

Referring to FIG. 4D, a wearable version 329 of the calibrated measurement device 300 includes a machine vision camera 331, a lead from force sensing resistor FSR 333, and a glass support 335 wrapped in a transparent strap 336. A red LED array 337 is inside the transparent strap 336, and an air pump actuated balloon 339 is attached with a primary MPF sensor. Independently adjustable red and green LED regulators 341, 343 are further included in the wearable version 329, as well as a USB 3.0 camera 345 for capturing video images.

Figure 5A:
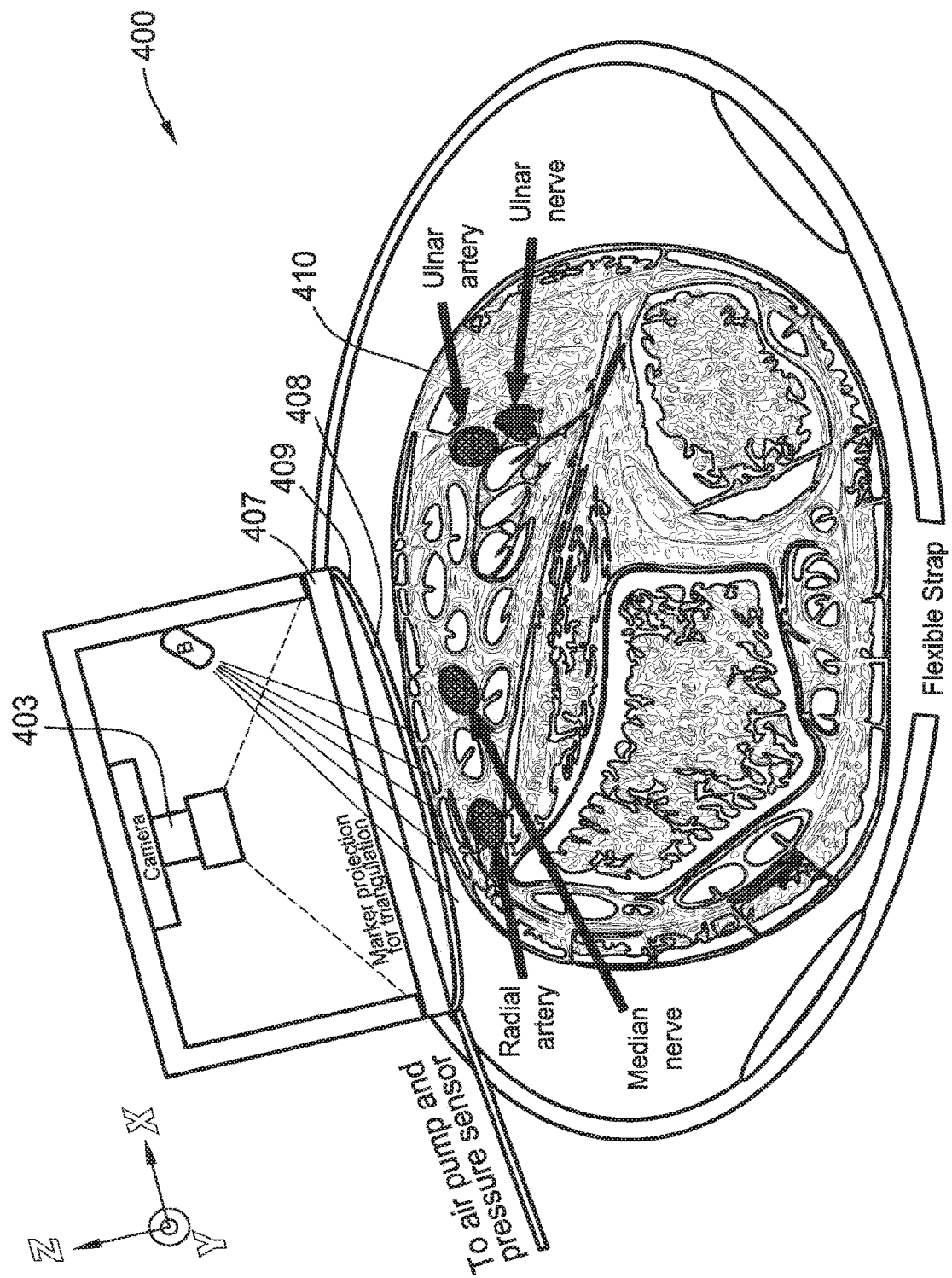
FIG. 5A is a cross-sectional illustration showing components of a calibrated measurement device including optical markers, according to another embodiment of the present disclosure.
Figure 5C:
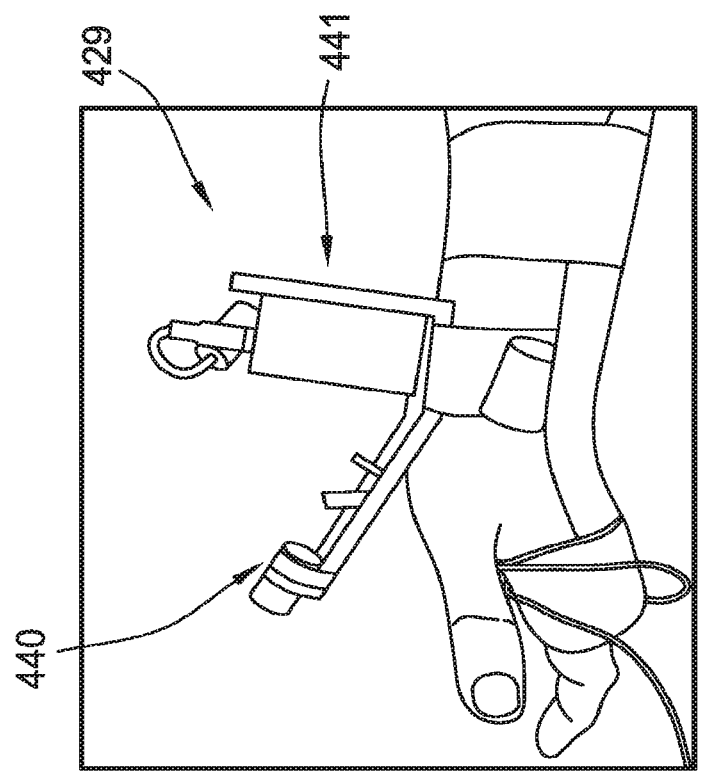
FIG. 5C is a perspective view illustrating a wearable version of the calibrated measurement device of FIG. 5A.
Figure 5B:
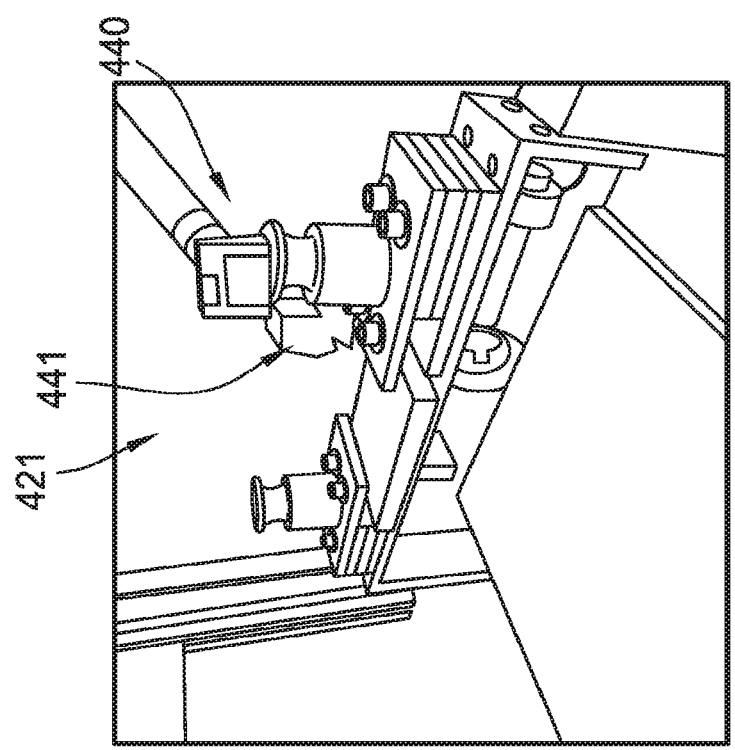
FIG. 5B is a perspective view illustrating a bench-top version of the calibrated measurement device of FIG. 5A.

Referring to FIG. 5A, a TBPI is in the form of another exemplary calibrated measurement device 400 in which a sensor array 408 is implemented based on structured light with projected light patterns (such as stripes) or optical markers (such as dots or holes) on the inside or outside surface of 408 that is in contact with the skin surface 410 (or, for example, directly on the skin surface 210). The movement of these patterns or markers is captured by a camera 403 that may also be placed at a different position and orientation than what is shown in FIG. 5A. In this embodiment, which is similar to but not necessarily identical to the embodiments described above, the sensor array 408 is implemented based on triangulation of optical patterns or markers on a sensing surface 409 (which is an outer surface of the sensor array 408) or the inside surface of the sensor array 408 (or, for example, directly on the skin surface 210). Based on the data from the camera placed appropriately to capture the images of the patterns or markers on a surface in contact with a skin surface 410 or directly on the skin surface 210, the deformation along the Z-axis is captured from the motion of the markers in the XY plane. Thus, the change of curvature in the ZX plane is sensed through the marker movement in the X-axis, as viewed by the camera 403. The calibrated measurement device 400 optionally includes one or more components of any of the other exemplary calibrated measurement device described in this disclosure. Referring further to FIGS. 5B and 5C, a benchtop version 421 and a wearable version 429 include a projector 440 and a machine vision camera 441.

Figure 6A:
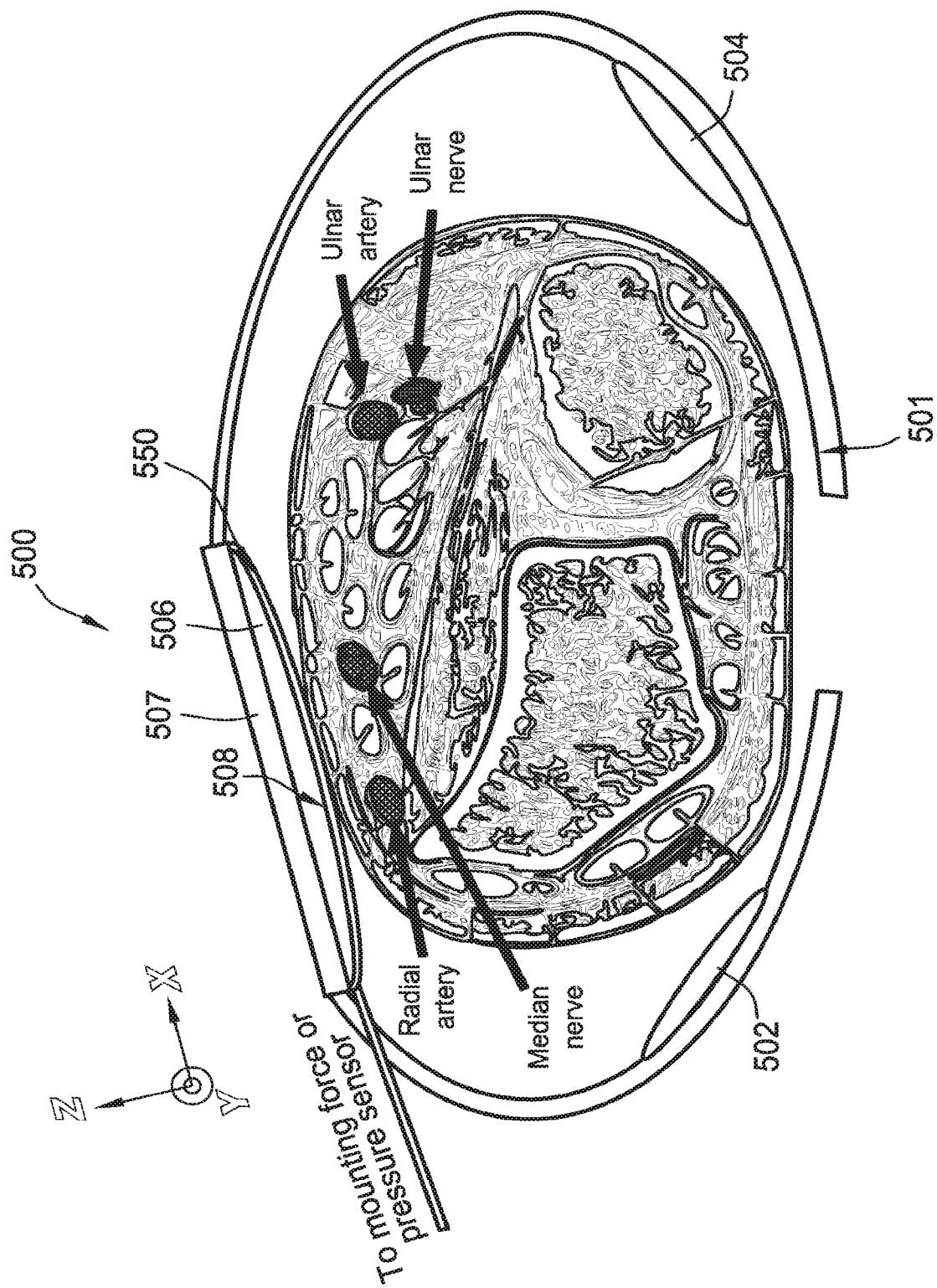
FIG. 6A is a cross-sectional illustration showing components of a calibrated measurement device including piezoelectric sensors, according to another embodiment of the present disclosure.
Figure 6B:
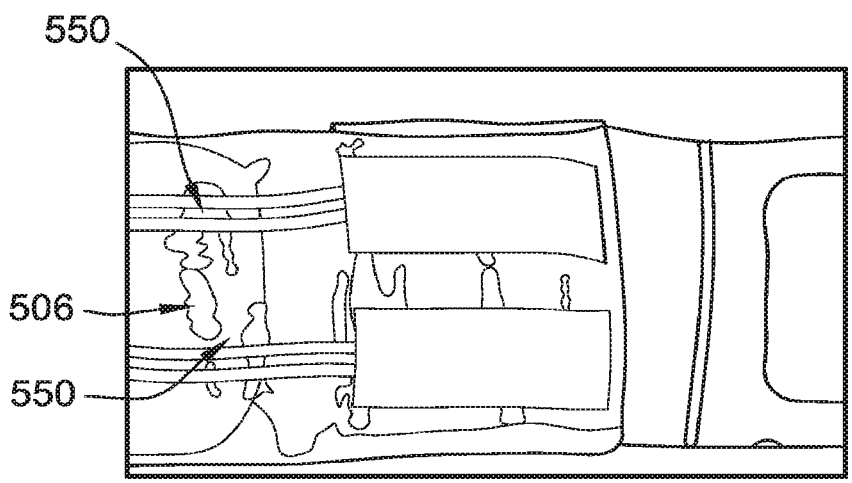
FIG. 6B is a perspective view illustrating the piezoelectric sensors of the calibrated measurement device of FIG. 5A attached to a balloon undersurface.
Figure 6C:
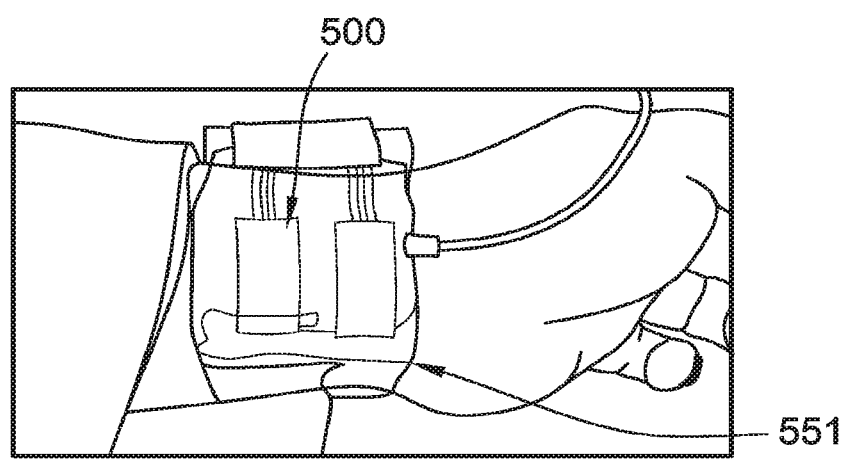
FIG. 6C is a perspective view illustrating the calibrated measurement device of FIG. 5A mounted on a wrist.

Referring to FIG. 6A, a TBPI is in the form of another exemplary calibrated measurement device 500 in which a sensor array 508 is implemented based on discrete force or displacement sensors 550. Specifically, the sensor array 508 is implemented by assembling discrete force or deformation sensors 550 such as resistive, piezoelectric, or capacitive elements 550. The calibrated measurement device 500 is similar, but not necessarily identical, to one or more of the other exemplary calibrated measurement devices described. For example, the calibrated measurement device 500 includes a flexible strap 501, a strap force sensor 502, a strap control balloon 504, and a blood-flow control balloon 506 supported on a rigid support 507. Referring further to FIG. 6B, the sensors 550 are attached to the undersurface of the blood-flow control balloon 506. Referring further to FIG. 6C, the calibrated measurement device 500 is mounted on a wrist 551.

Optionally, the discrete sensors described above can be made of a thin film of piezoelectric polymer, such as polyvinylidene fluoride (PVDF), with both sides coated with silver ink acting as electrodes. The electrodes are further coated with an insulating material to avoid electrical conduction between the skin and the sensor. The thickness of the sensing element is kept thin enough to achieve good mechanical coupling with the skin. In the simplest arrangement, only two sensing elements are used, one for the detection of proximal pulsation and the other for distal. The number of elements can be increased to extract more complex markers if necessary. The signals from the sensor are passed through the signal conditioner and fed to the TBPI processor. These two proximal and distal signals from piezo film sensors can be equivalently treated as IAH described above for the purpose of BP estimation.

Figure 7B:
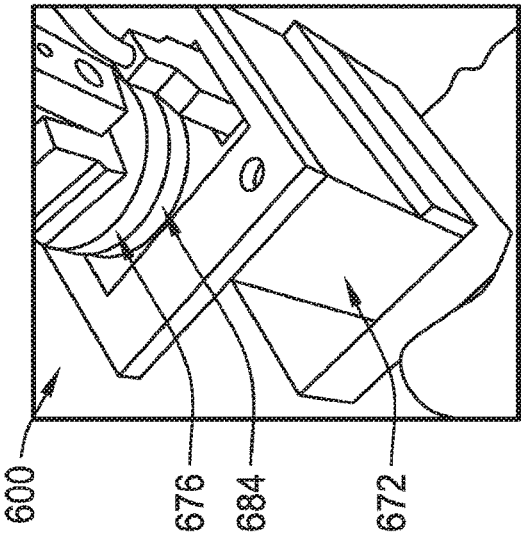
FIG. 7B is an enlarged perspective illustration showing an experimental setup for a pig model.
Figure 7C:
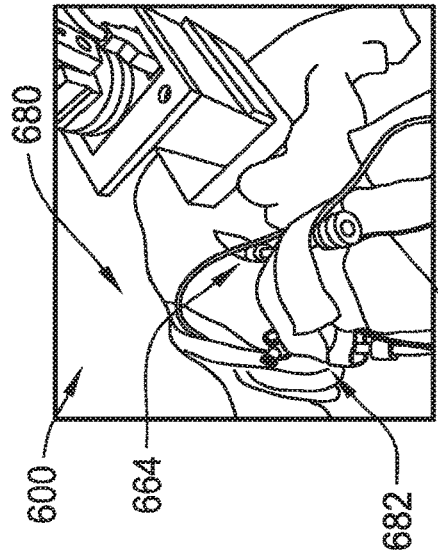
FIG. 7C is a perspective illustration showing an overall view of the experimental setup of FIG. 7B.
Figure 7A:
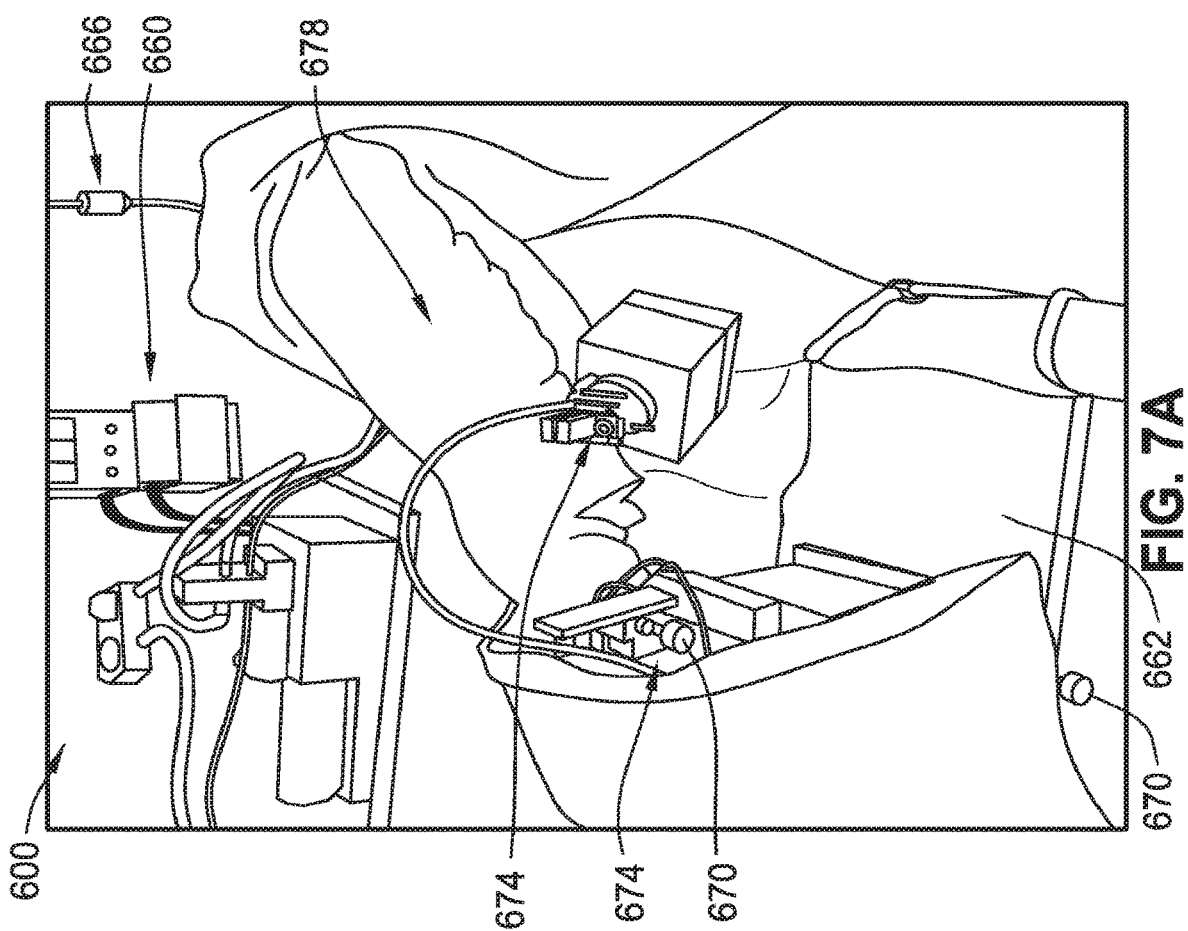
FIG. 7A is perspective illustration showing an animal experiment with a rabbit model.

Referring to FIGS. 7A-7C, an experimental setup 600 shows animal experiment for a rabbit model (FIG. 7A) and a pig model (FIGS. 7B and 7C). The setup 600 includes an anesthesia apparatus 660, a back support 662, a catheter 664 to access artery, and a drug and saline drip 666. The setup 600 further includes an optical fiber 668 connected to a tip of a fiberoptic pressure sensor (e.g., from FISO), a height adjustment control 670 of a 6-DoF positioner, a version of TBPI 672, a position lock 674, a 6-DoF force sensor 676 (e.g., from ATI). The setup 600 also includes the anesthetized pig 678, the anesthetized rabbit 680, TPS 682 from ICU Medical, and a $6^{th}$ DoF (Zrot) 684 added to the positioner for animal experiment.

According to an alternative exemplary embodiment, a sensor array measures movement of an arterial wall directly. For example, in this embodiment ultrasonic sensing elements of the sensor array directly measure a curvature of a targeted blood vessel, instead of its impression on the skin surface. This embodiment optionally includes one or more components of any of the disclosed calibrated measurement devices, with the modification of having at least one ultrasonic sensing element on the sensor array.

According to another alternative exemplary embodiment a sensor is coupled to a mechanical stage and is used for varying a mounting force (e.g., in a bench top device). In this embodiment, instead of using a blood-flow control balloon, the mounting force is adjusted with the help of a mechanical stage that is coupled with force and/or displacement sensors.

Thus, in accordance with the disclosed embodiments, the spatio-mechanical state of the skin in the BPI is measured by a sensor array, such as the sensor arrays disclosed above. The sensor array includes, for example, an optical sensor (e.g., photometric stereo or structured light) as described above. In other examples, ultrasound imaging and/or tactile sensor arrays are used instead of or in addition to the optical sensor. The sensor array is positioned above an artery, with the radial artery being one example of the artery.

Varying skin pressure is applied with an external device coupled with a force sensor. The sensor arrays described above are some examples of the force sensor, while the external device includes the blood-flow control balloons. The spatio-temporal variation in the contact force and/or geometry is recorded as the skin pressure is varied. The characteristic spatio-temporal signals corresponding to systolic and diastolic pressure are determined. Examples of the characteristic spatio-temporal signals include contrasting between upstream and downstream as described above or maximal pulsation. The determined values of the characteristic spatio-temporal signals are used to calibrate the measurement device, and the calibration is used to estimate blood pressure continuously by analyzing the continuous spatio-temporal signal. For improved continuous monitoring, an optical sensor for an oscillometric method provides beneficial results.

According to one exemplary benefit of the present disclosure, the disclosed device and method for monitoring intra-arterial blood pressure eliminates the need for an intrusive limb-encircling pressure cuff and high pressures needed to occlude the target artery, while simultaneously occluding lymphatics, veins and other arteries and, thus, cutting off blood circulation in the limb (e.g., arm). For example, during the calibration phase of the disclosed BPI, while the radial artery may be occluded by the blood-flow control balloon, the blood circulation due to ulnar artery, veins, and lymphatics remains intact.

According to another exemplary benefit of the present disclosure, the disclosed device and method for monitoring intra-arterial blood pressure provides an instantaneous blood pressure vs. time tracing continuously based on direct observation of blood pressure on skin geometry. The continuous tracing is obtained without relying on models derived from indirect empirical correlations or trademarked proprietary algorithms that cannot be independently validated or critiqued scientifically.

According to yet another exemplary benefit of the present disclosure, the disclosed device and method for monitoring intra-arterial blood pressure facilitates direct derivation of SBP, MAP, and/or DBP from the continuous blood pressure vs. time trace for each heartbeat. A further benefit is that the disclosed device and method measure blood pressure over multiple heart beats and respiratory cycles to provide more accurate measure of blood pressure and valuable information on beat-to-beat blood pressure variability. Yet another benefit is that the disclosed device and method provides additional data of clinical interest such as heart rate, heart rhythm, respiratory rate, reparatory pattern and apnea.

According to a further benefit of the present disclosure, the device for monitoring intra-arterial blood pressure is a wearable device that is integrated with existing mobile phones. Data is transferred between the device and a mobile phone instantly over low-bandwidth cellular connection for online/remote management of hypertension.

According to further benefits of the present disclosure, the disclosed device and method for monitoring intra-arterial blood pressure provides continuous ambulatory blood pressure monitoring that identifies abnormal blood pressure patterns, including white coat hypertension, masked hypertension, non-dipping or increase in blood pressure during sleep and the morning blood pressure surge. The monitoring further provides an accurate assessment of treatment effectiveness and improved tailoring of therapy, identifies lifestyle motivations needed to lower patients' blood pressure (e.g., reducing smoking and stress), and provides graphical feedback to review with patients and which aids in patient compliance with treatment.

According to other benefits of the present disclosure, the disclosed device and method provides a 24-hour reliable beat-to-beat monitoring of blood pressure for use in acute hospital settings as an alternative to invasive (using intra-arterial catheters) monitoring. Additionally, other benefits of include affordability, based on the BPI being optionally built from off-the-shelf manufactured components, and lack of requirement for an additional power source, based on the BPI being optionally battery-driven.

The disclosed device and method is further useful for other purposes, including, for example, blood draw or catheter insertion. For example, a device for such exemplary purposes includes the flexible strap, the strap force sensor, the strap control balloon, and/or the blood-flow control balloon. Optionally, optical sensors or other skin surface sensing elements as disclosed above are used to augment and improve the performance of calibrated measurement devices. Optionally, yet, specific combinations of the flexible strap, sensing means (optical, ultrasound, capacitance-based tactile array, etc.), calibration method, and blood pressure monitoring are optimally implemented depending on the artery location (radial, brachial, etc.), purpose (monitoring for well-being, screening, emergency care, etc.), and setting (hospital, home, wearable, etc.).

While the present invention has been described with reference to one or more particular embodiments, those skilled in the art will recognize that many changes may be made thereto without departing from the spirit and scope of the present invention. Each of these embodiments and obvious variations thereof is contemplated as falling within the spirit and scope of the invention. It is also contemplated that additional embodiments according to aspects of the present invention may combine any number of features from any of the embodiments described herein.

What is claimed is:

1. A method for continuously, non-invasively, and directly measuring blood pressure, the method comprising:
   providing a calibrated measurement device having a frame with a first side and a second side, a balloon mounted to the second side, an optical system between the first side and the balloon, and a sensor array having a sensor surface;
   placing the sensor array in a non-invasive manner over a skin surface connected to an artery by adjoining soft tissues;
   inflating the balloon with a controlled amount of pressure;
   in response to the inflating of the balloon, detecting signals, via the optical system and the sensor array, caused by changes in artery size and shape during a heartbeat cycle; and
   measuring and processing, via a controller, the signals to determine blood-pressure parameters.

2. The method of claim 1, wherein the signals detected via the optical system are responsive to visible deformations in the sensor surface, and wherein the visible deformations in the sensor surface are caused by deformations in the skin surface, the deformations being caused by the changes in artery size and shape during a heartbeat cycle.

3. The method of claim 2, wherein the sensor array further comprises capacitance-based tactile sensors, and wherein the signals are tactile deformations in the sensor surface, the tactile deformations in the sensor surface being caused by deformations in the skin surface, the deformations being caused by the changes in artery size and shape during a heartbeat cycle.

4. The method of claim 2, wherein the optical system further includes a camera capable of detecting the signals.

5. The method of claim 2,
   wherein inflating the balloon further includes a controlled increase and a controlled decrease of a pressure in the balloon;
   wherein detecting signals further includes segmentation of a pulsation area of the artery and generating at least one marker;
   wherein measuring further includes measuring at least one pressure in the balloon; and
   wherein processing further includes mapping the at least one pressure at which the at least one marker reaches a threshold to one or more of a systolic blood pressure, mean arterial pressure, or diastolic blood pressure.

6. The method of claim 1, wherein the calibrated measurement device further includes a rigid support adjacent to the balloon and between the optical system and the sensor array; and wherein the rigid support is transparent and the balloon is transparent.

7. The method of claim 1, wherein the sensor surface further includes a reflective layer in contact with the skin surface and responsive to deformations in the skin surface.

8. The method of claim 1, further comprising determining the changes in the artery size and shape based on an ultrasound of the artery.

9. The method of claim 1, further comprising placing the sensor surface in direct contact with the skin surface.

10. The method of claim 9, further comprising coating the skin surface with a pigment prior to placing the sensor surface in direct contact with the skin surface.

11. A calibrated measurement device for continuously, non-invasively, and directly measuring blood pressure, the calibrated measurement device comprising:
   a frame:
   a strap;
   a balloon coupled to an internal surface of the strap, the balloon having an inflated state in which a controlled amount of pressure isolates a signal from an artery without compromising venous and lymphatic circulation or flow in other arteries of a limb containing the artery;
   a camera mounted to the frame and spaced from the balloon; and
   a sensor array mounted on a surface of the balloon to directly contact a skin surface and non-invasively monitor blood pressure, the sensor array and the camera detecting deformations in the skin surface caused by changes in artery size and shape during a heartbeat cycle, the deformations in the skin surface corresponding to blood pressure.

12. The calibrated measurement device of claim 11, wherein the strap is removably attached to the limb.

13. The calibrated measurement device of claim 11, further comprising a transparent rigid support mounted to the strap, the balloon being mounted on the transparent rigid support; the transparent rigid support being positioned between the camera and the balloon.

14. The calibrated measurement device of claim 11, further comprising a strap control balloon coupled to the internal surface of the strap in a different area than the balloon, the strap control balloon having an inflated state in which a force applied between the skin surface of the limb and the strap is fine tuned.

15. The calibrated measurement device of claim 14, further comprising a strap force sensor coupled to the internal surface of the strap in a different area than the balloon and the strap control balloon, the strap force sensor detecting the force applied between the skin surface of the limb and the strap when at least one of the balloon and the strap control balloon is in the respective inflated state.

16. The calibrated measurement device of claim 11, wherein the sensor array further includes an array of capacitance-based tactile sensors.

17. The calibrated measurement device of claim 11, wherein the sensor array further includes one or more resistive, piezoelectric, or capacitive elements.

18. A method for continuously, non-invasively, and directly measuring blood pressure in an artery, the method comprising:
- providing a calibrated measurement device having a strap for mounting on a limb, the strap having mounted on its internal surface a balloon, a strap control balloon, and a strap force sensor, the balloon having mounted on its internal surface a sensor array, the strap further having a frame with a first side and a second side, the balloon being mounted to the second side, the strap further having an optical system between the first side and the balloon;
- placing the strap over a limb such that the sensor array is in contact with a skin surface over an artery in a non-invasive manner;
- inflating the balloon with a controlled amount of pressure without compromising venous and lymphatic circulation or flow in other arteries of the limb containing the artery;
- in response to inflating the balloon, detecting signals, via the optical system and the sensor array, caused by changes in the artery size and shape during a heartbeat cycle;
- inflating the strap control balloon with a controlled amount of pressure to apply a tension force between the strap and the skin surface of the limb;
- based on detection by the sensor array and the strap force sensor, fine-tuning pressure applied by at least one of the balloon or the strap control balloon to enhance detection of the signals; and
- measuring and processing, via a controller, the signals to determine blood-pressure parameters.

19. The method of claim 18, further comprising, in response to the signals, measuring at least one of a deformation of the skin surface or forces within and on the skin surface.

20. The method of claim 18, further comprising determining the changes in the artery size and shape and changes in soft tissues adjoining the artery based on ultrasound.

* * * * *